United States Patent [19]
Neipel et al.

[11] Patent Number: 5,827,519
[45] Date of Patent: Oct. 27, 1998

[54] HUMAN HERPESVIRUS TYPE 6 PROTEIN P100, THE CORRESPONDING DNA SEQUENCES, THEIR PREPARATION AND USE

[75] Inventors: Frank Neipel, Erlangen; Bernhard Fleckenstein, Wiesenthau, both of Germany

[73] Assignee: Behring Diagnostics GmbH, Marburg, Germany

[21] Appl. No.: 467,527

[22] Filed: Jun. 6, 1995

Related U.S. Application Data

[62] Division of Ser. No. 266,311, Jun. 27, 1994, which is a continuation of Ser. No. 126,435, Sep. 24, 1993, abandoned, which is a continuation of Ser. No. 908,041, Jul. 6, 1992, abandoned.

[30] Foreign Application Priority Data

Jul. 8, 1991 [EP] European Pat. Off. ............... 91111338

[51] Int. Cl.$^6$ .................... A61K 39/245; C12Q 1/70; G01N 33/569; C07K 16/08
[52] U.S. Cl. ..................... 424/231.1; 435/5; 435/7.1; 530/388.3; 530/389.4
[58] Field of Search ................... 530/387, 9, 388.3, 530/389.4; 424/159.1, 231.1; 435/5, 7.1

[56] References Cited

FOREIGN PATENT DOCUMENTS 4013526  11/1990  Germany .
WO 91/02794  3/1991  WIPO .

OTHER PUBLICATIONS

Littler et al., Indentification, Cloning, and Expression of the Major Capsid Protein Gene of Human Herpesvirus 6, Journal of Virology, vol. 64, No. 2, Feb. 1990, pp. 714–772.

Larcher et al., Serological Crossreaction of Human Herpesvirus 6 with Cytomegalovirus, The Lancet, Oct. 22, 1988, pp. 963–964.

Neipel et al., The Unique Region of the Human Herpesvirus 6 Genome is Essentially Collinear With the $U_L$, Segment of Human Cytomegalovirus, Journal of General Virology (1991), 72, pp. 2293–3397.

Chang et al., Identification, Characterization, and Sequence Analysis of a cDNA Encoding a Phosphoprotein of Human Herpesvirus 6, Journal of Virology, vol. 65, No. 6, Jun. 1991, pp. 288–2894.

Lawrence et al., Human Herpesvirus 6 Is Closely Related to Human Cytomegalovirus, Journal of Virology, vol. 64, No. 1, Jan. 1990, pp. 287–299.

Josephs et al., Genomic Analysis of the Human B–Lymphotropic Virus (HBLV), Science, vol. 234, (Oct. 31, 1986) pp. 601–603.

Neipel et al., Gene for the Major Antigenic Structural Protein (p100) of Human Herpesvirus 6, The Journal of Virology, vol. 66, No. 6, (Jun. 1992), pp. 3918–3924.

Yamamoto et al., Identification of a Nucleocapsid Protein as a Specific Serological Marker of Human Herpesvirus 6 Infection, Journal of Clinical Microbiology, vol. 28, No. 9, Sep. 1990, pp. 1957–1962.

*Primary Examiner*—James Ketter
*Assistant Examiner*—John S. Brusca
*Attorney, Agent, or Firm*—Finnegan, Henderson, Farabow, Garrett & Dunner, L.L.P.

[57] ABSTRACT

The invention relates to the human herpesvirus type 6 protein p100 and parts thereof having its specific immunological properties. It further relates to antibodies directed to them and to the corresponding DNA sequences. They can be used in pharmaceutical or diagnostic compositions, optionally together with other HHV-6 proteins or the corresponding DNA sequences.

8 Claims, 11 Drawing Sheets

SEQUENCES OF THE VIRAL INSERTS OF CLONES pMF94 AND pMF295. BOTH SEQUENCES ARE PART OF THE MAJOR CAPSID PROTEIN GENE OF HHV-6 AS PUBLISHED IN (LITTLER ET AL. 1990).

NUCLEOTIDE SEQUENCE OF pMF94

```
  1  GAATTCCTGA CGCCAGCGCC ACAGGCCTTG TTATTTGATA GTGCCGGGAG
 51  TACGCAGAAG TAAAATATCT TGCTCAGGAT GGTGGTTTCG TTCGATGGTC
101  TGTCATTGTC GGTAAAGACG ACGCTTGAAT CTATTAGATT CATTCTTTGC
151  ACATCGGATA TTTCGTAATT TCTAACTCTT ACGGTGTTCT GTGTCAGTGG
201  TGTATCATCC GCTGTTATTT TTGCATTCGT GTCGTTTCTG GGCATGGTAT
251  GGACGAACGG GCAGAACAGA CGTCCGTCGA ACAACGCGTT GGCGAAATTC
301  ACCAGAGGTT CGCCGCAAAG TTGCTCGTTG AGGTTGGAGA TAGAGATTGT
351  TCTCTTCACT AGGCGAATTA GCGACACAAG ATTTCTGTAG TGAGCGAAAG
401  CTGCTCCCGG GATCAGTTCG TCGCCCATGT GGTTGGAATT C (SEQ ID NO: 5)
```

NUCLEOTIDE SEQUENCE OF pMF295

```
  1  CCGTGTGAAA TTAAACGACA CCATGGAAAA CAACCTACCC ACCAGCGTTT
 51  TTTTCCACAA TAAAGACCAA GTCGTGCAGC GAATTGATTT TGCCGACATA
101  TTACCGTCGG TTTGCCATCC CATTGTCCAC GACTCGACCA TCGTCGAACG
151  ACTCATGAAA AGCGAACCAT TGCCTACCGG CCACCGCTTT TCCCAACTAT
201  GTCAACTAAA AATTACCCG (SEQ ID NO:6)
```

FIG. 1

SEQUENCE OF THE VIRAL INSERT OF CLONE pMF90. THE
SEQUENCE IS IDENTICAL WITH NUCLEOTIDES 117-194 OF THE
SEQUENCE PUBLISHED IN (CHANG AND BALACHANDRAN, 1991).

```
  1       CCA CTTTTTGAAA GTTTTATGAA CATCATCTCG AATCCTGAGG
 51 TTACGAAGAT GTACATTCAG CATGATAGTG ATCTGTATAC GAGGGTTTTG
101 GTAACGGCTT CCGATACATG TACACAGGCG TCGGTTCCCT GTGTGCACGG
151 ACAAGAAGTG GTGCGAGACA CCGGGAGATC GCCGTTGAGG ATTGACCTTG
201 ATCATTCGAC CG (SEQ ID NO:7)
```

FIG. 2

COMPLETE SEQUENCE OF THE HHV-6 EcoRI FRAGMENTS NUMBERED
6 AND 7 (STARTING FROM THE LEFT END). THESE FRAGMENTS
CONTAIN THE ENTIRE p100 GENE OF HHV-6. THE POSITION
OF pROS EXPRESSION CLONES IS INDICATED WITHIN THE
SEQUENCE.

```
    E
    c
    o
    R
    I
  GAATTCCTATGTTNCGCCCCGTGCTAGATGTTTTACTTTCAGTCTTTTTACGCCGGTGTAAGGTTTTGTACC
1-----------------------------------------------------------------------72
  TGATAGTTGCGATTATAGCTAGCATGCTTATACTATATGAACAGACTGCATGATAGATGAAGTAAACTAACT
73----------------------------------------------------------------------144
  GACAGAAAAAACGGTTGAATGAGAACAGTTGCTTTCTGTTCACTGTCATAAAAAAGACACACCACATGAGCA
145---------------------------------------------------------------------216
  CAAAATCGCTAGCAAAGAGTGTGATGACGTAAAATGAAGTAGCGTTATGTTTTGCGACTCTGTGGTAGAGAA
217---------------------------------------------------------------------288
  TCATGGTGGTAACCACTATAATGATCATGGGGATAGATGTGGTGAGCGTGATTCCGGTAACTGCGCTCTCCA
289---------------------------------------------------------------------360
  TGATTCGTGCTGTCTTTAGCGTGGGTGTCGAGGTACAGGAAGCATTGCCTTTGAACTCTTCATTGCGCTATT
361---------------------------------------------------------------------432
  AAAGATATTGAATGTTATTTTCATGTTACGCTACATTAAAATATTCGGTAACAATGATGTCTGAAGACTTAC
433---------------------------------------------------------------------504
  CAGAAGTTTGGACAGCTCAATGACAGTGTCCATCTCGTCGCTTGTCAGTTTTCTGTGTGGGTAAAAAAAAGA
505---------------------------------------------------------------------576
  CTATTAAACATTGAATGTTGGCGGAAATGAGCAGTTCTGTTTTTGAGTTTGTTTTCTAAAATATGGATCTGC
577---------------------------------------------------------------------648
                                                            M  D  L  Q-
  AAAGACATCCGATTCCGTTTGCGTGGCTAGATCGAGACAAAGTTGAGCGTCTTACAGATTTTCTCAGCAATT
649---------------------------------------------------------------------720
    R  H  P  I  P  F  A  W  L  D  R  D  K  V  E  R  L  T  D  F  L  S  N  L-
  TGGAAAGACTGGATAATGTAGATTTGCGAGAGcaTCCCCATGTGACTAATTCTTGTGTCGTGAGAGAGGGAG
```

FIG. 3-1

```
722----------------------------------------------------------------------792
     E  R  L  D  N  V  D  L  R  E  H  P  H  V  T  N  S  C  V  V  R  E  G  D-
                 D
                 r ----BEGIN OF pDF446-4
                 a
                 I
     ACGATGTAGACGATTTAAAAACATTGTATAACCTACTAGTGTTATGGCTTATGTATCACTACGTCTTATCTA
793----------------------------------------------------------------------864
     D  V  D  D  L  K  T  L  Y  N  L  L  V  L  W  L  M  Y  H  Y  V  L  S  K-
     AAAGGAAGCCGGATTATAATGCTATATGGCAAGACATCACGAAACTCCAAAGTGTCGTAAACGAGTACTTAA
865----------------------------------------------------------------------936
     R  K  P  D  Y  N  A  I  W  Q  D  I  T  K  L  Q  S  V  V  N  E  Y  L  N-
     ACTCCAAGGTCTGAATAAAGGAATTTTTGAAAAATATGTTCACGAACAAAGAAAAGTTTGAATCGCAATTCA
937---------------------------------------------------------------------1008
     S  K  G  L  N  K  G  I  F  E  N  M  F  T  N  K  E  K  F  E  S  Q  F  S-
     GTGATATTAATCGCGCTTTACTGCGTTTAGGAAACTTTATTAAGTGGGGTAGCAATGTTGCGATCGATACTC
1009---------------------------------------------------------------------1080
     D  I  N  R  A  L  L  R  L  G  N  F  I  K  W  G  S  N  V  A  I  D  T  P-
     CTTATGTAAATCTTACTGCAGAAGACAGCAGCGAGATAGAAAATAATTTGCAAGATGCTGAAAAAAACATGC
1081---------------------------------------------------------------------1152
     Y  V  N  L  T  A  E  D  S  S  E  I  E  N  N  L  Q  D  A  E  K  N  M  L-
     TGTGGTATACCGTCTATAACATAAATGACCCCTGGGACGAAAACGGTTACTTAATAACGAGTATTAATAAAT
1153---------------------------------------------------------------------1224
     W  Y  T  V  Y  N  I  N  D  P  W  D  E  N  G  Y  L  I  T  S  I  N  K  L-
     TAATTTATCTCGGTAAGTTATTTTTAGCGTTAACTCAGTCCTGGTCAAAGCTAGAAAAGGTTGCTATGAGTC
1225---------------------------------------------------------------------1296
     I  Y  L  G  K  L  F  L  A  L  T  Q  S  W  S  K  L  E  K  V  A  M  S  Q-
     AAATTGTAATCACGCAAAATCATCTCTCGGGTCATTTGAGGAGGCACGACAATTTTAATATTGTATATTCTC
1297---------------------------------------------------------------------1363
     I  V  I  T  Q  N  H  L  S  G  H  L  R  R  H  D  N  F  N  I  V  Y  S  H-
     ATAGGGTTTTGCAGACTCCTCTGACTGGTCAAAGAGTAGAGAGTTTTCTGAAAATAATCACCAGTGATTATG
1369---------------------------------------------------------------------1440
     R  V  L  Q  T  P  L  T  G  Q  R  V  E  S  F  L  K  I  I  T  S  D  Y  D-
                                                                         H
                                                                         a
                              END OF pDF446-4----- e -BEGIN
                                                   I  OF
                                                   I  pD2Hae
                                                   I
     ATATTATCAAAAGTAGTCTGGAATCACACAGCGCGTCGAAAGCATTTTCGATGTCTGAGATTGGGCCTAATT
1441---------------------------------------------------------------------1512
```

FIG. 3-2

```
     I  I  K  S  S  L  E  S  H  S  A  S  K  A  F  S  M  S  E  I  G  P  N  S-
     CTTTAATGGATTTCGTCCCTTTACGCGGCGATATACATTCAAATTTGACTTTACCTAGTATGTCTATAGATA
1513------------------------------------------------------------------------1584
     L  M  D  F  V  P  L  R  G  D  I  H  S  N  L  T  L  P  S  M  S  I  D  T-
     CAAAGAAATCATCTTTAGATCCGGCTCGTCTGAAAAAAGTAATTCCAGAAGTTTGGATAGTTTCTTAAGAA
1585------------------------------------------------------------------------1656
     K  K  S  S  L  D  P  A  R  L  K  K  S  N  S  R  S  L  D  S  F  L  R  M-
     TGCAGAGACAACCTAAATTTCTAGAGTTGGATAGCGTTGATAATGCCGGGGAAAAAATTTTACTAAAGGAAG
1657------------------------------------------------------------------------1728
     Q  R  Q  P  K  F  L  E  L  D  S  V  D  N  A  G  E  K  I  L  L  K  E  A-
     CAACACTCGGGGGTGAAAACGTTAAAGCGACAACGCCTGCTTCCTCTGTCTCTTTAATGTCCGGAGTTGAGT
1729------------------------------------------------------------------------1800
     T  L  G  G  E  N  V  K  A  T  T  P  A  S  S  V  S  L  M  S  G  V  E  S-
     CGCCGTCGTCTTTCACTTCTACCAATCTGGATCTGCCGTTGTCGTCTTTCACTTCTACTAATCTGGATCTGC
1801------------------------------------------------------------------------1872
     P  S  S  F  T  S  T  N  L  D  L  P  S  S  F  T  S  T  N  L  D  L  R-
                                  H
                                  a
           END OF pD2Hae ----- e ------BEGIN OF pDF446-3
                                  I
                                  I
                                  I
     GAGATAAGTCGCACGGTAATTATAAAATTGGCCCTTCGGGGATTTTAGATTTTAATGTTAAATTTCCACCTA
1873------------------------------------------------------------------------1944
     D  K  S  H  G  N  Y  K  I  G  P  S  G  I  L  D  F  N  V  K  F  P  P  N-
     ATGCGCAATTGAATACGAACGGTGTGGATTTACTACAGGATAAAACTTCGATCGGGAGTCCCAGTAGCGGTA
1945------------------------------------------------------------------------2016
     A  Q  L  N  T  N  G  V  D  L  L  Q  D  K  T  S  I  G  S  P  S  S  G  I-
     TTACCGATGTGGTAAATGGTTTCGCTAATCTCAATCTGCATCAGAATAAATCAAATGTTTCGCCACCGTGGA
2017------------------------------------------------------------------------2088
     T  D  V  V  N  G  F  A  N  L  N  L  H  Q  N  K  S  N  V  S  P  P  W  S-
     GCAGAAACACAGCGGCGAATGCGGACTTTTTAGATCCGGTGCATCGCTTTGTTCCTGAGCAGACAGGGACAC
2089------------------------------------------------------------------------2160
     R  N  T  A  A  N  A  D  F  L  D  P  V  H  R  F  V  P  E  Q  T  G  T  P-
     CCTTCGTGTTGAATAATTCCGACGTGGCGGGATCAGAAGCGAAGCATACGACTTACAGTACGGAGACCGGCG
2161------------------------------------------------------------------------2232
     F  V  L  N  N  S  D  V  A  G  S  E  A  K  H  T  T  Y  S  T  E  T  G  V-
     TTTCACCCCGTAACGTTTTTCTCATTAAAGATTTGAGAGGCAAAGACGGTTTTAGGAAACAGAAGCAGTCAG
2233------------------------------------------------------------------------2304
     S  P  R  N  V  F  L  I  K  D  L  R  G  K  D  G  F  R  K  Q  K  Q  S  D-
     ATATTCCGAAAAGCTTAACTAAGGAAAGAAATGATAAAGCTATAATGCACTCACGCGAGGTGACCGGAGATT
2305------------------------------------------------------------------------2376
```

*FIG. 3-3*

```
              I  P  K  S  L  T  K  E  R  N  D  K  A  I  M  H  S  R  E  V  T  G  D  S-
                                               E
              END OF pDF446-3----              c  ---- BEGIN OF pD2Hind
                                               o
                                               R
                                               I
        CTGGCGATGCGACTGAAACTGTGGGTGCTCGGAATTCCCCGGCGTTGAGAAAAATTAAGCAAGCAAATGATT
     2377--------------------------------------------------------------------------2448
              G  D  A  T  E  T  V  G  A  R  N  S  P  A  L  R  K  I  K  Q  A  N  D  F-
        TTTTTGCCGGGTTAAATAAGAAAAATGATCGTGACGTATTAAGAGGGGGGAAAGGAAATAGCAAGGACTTGC
     2449--------------------------------------------------------------------------2520
              F  A  G  L  N  K  K  N  D  R  D  V  L  R  G  G  K  G  N  S  K  D  L  H-
        ATTCTGGCGGCAATGCAAAAAAAAAGAAATGTCGGGAAAGTTTAATGACGATAAAGAAATGACGCGAAACG
     2521--------------------------------------------------------------------------2592
              S  G  G  N  A  K  K  K  E  M  S  G  K  F  N  D  D  K  E  M  T  R  N  G-
        GACAAGAGCCATCACGTAGTTTAATGGGAGATGCTAGAAATGCCGGAGATGAACAATATATTCAAGCGGGTC
     2593--------------------------------------------------------------------------2664
              Q  E  P  S  R  S  L  M  G  D  A  R  N  A  G  D  E  Q  Y  I  Q  A  G  L-
        TCGGGCAGCGAGTTAACAATCTTCTAAGTCAATTTACAAATCTGATTAGTTTAGGCGAGAAGGGCATCGAAG
     2665--------------------------------------------------------------------------2736
              G  Q  R  V  N  N  L  L  S  Q  F  T  N  L  I  S  L  G  E  K  G  I  E  D-
        ACATTTTGCAGAATCAGCGCGGGACCGAGTTAAAGTTGGCTACAGAAAACAAGTCGGGACGCGAATCGGAGG
     2737--------------------------------------------------------------------------2808
              I  L  Q  N  Q  R  G  T  E  L  K  L  A  T  E  N  K  S  G  R  E  S  E  E-
        AAGCTAACGTAGAAAAAATTCTTGAAGTTAGTAATCCTCAAGATATGTTTAAAAATTTTAGGTTGCAAAACG
     2809--------------------------------------------------------------------------2880
              A  N  V  E  K  I  L  E  V  S  N  P  Q  D  M  F  K  N  F  R  L  Q  N  D-
        ATCTCGATTCCGTTCAGTCTCCGTTTAGGCTACCGGATGCTGATTTGTCTCGCGAGTTAGATTCCGCGTCAT
     2881--------------------------------------------------------------------------2952
              L  D  S  V  Q  S  P  F  R  L  P  D  A  D  L  S  R  E  L  D  S  A  S  F-
                              H
        END OF pD2Hind -----  i
                              n
                      BEGIN   d
                      OF pMF101R  I
                              I
                              I
        TTAAGGACGCGTTAGACTTGAAGCTTCCGGGTAACGGAGAACGAGAAATAGATCTCGCTCTTGAAAAAGTGA
     2953--------------------------------------------------------------------------3024
              K  D  A  L  D  L  K  L  P  G  N  G  E  R  E  I  D  L  A  L  E  K  V  K-
```

FIG. 3-4

```
AGGTAGGCGAGACGGAAACCTCAGATTTAAAAGTCGGTCAGGATGAAAGTTTTGTTCCTGCGCAATTAATGA
3025------------------------------------------------------------------3096
     V  G  E  T  E  T  S  D  L  K  V  G  Q  D  E  S  F  V  P  A  Q  L  M  K-
                          END OF pMF101R ────┐
                                             │

AGGTTGAGACACCTGAAGAAAAAGATGATATAATTGAACAGATGGTTCTGAGGATACGTCAAGACGGGGAAA
3097------------------------------------------------------------------3168
   V  E  T  P  E  E  K  D  D  I  I  E  Q  M  V  L  R  I  R  Q  D  G  E  T-
CTGATGAAAACACCGTCTCTGGGCCGGGAGTCGCTGAGTCTTTGGATATAGAAGCCAAAGGCGAGTCAGCGA
3169------------------------------------------------------------------3240
   D  E  N  T  V  S  G  P  G  V  A  E  S  L  D  I  E  A  K  G  E  S  A  I-
TCGCGTCGTGATGTAAAAAATTTTCTCTGGGGAGTTTCAGGTTGCCAATAAAATGCCCATTCTCAGACAGCT
3241------------------------------------------------------------------3312
   A  S  *
TTGCGATTACGTCTTTTTGTTCATTGTTCTGGCTTGTCATTCTTTCTACATAAAACAGGGTCGCGATAGGTG
3313------------------------------------------------------------------3384
TGCTTTGAGGCAGGATCAGATTTGGAGAAAATGAACGCAGCGTAATGTGCAAAGGTGTTCCCGGGGCCCACA
3385------------------------------------------------------------------3456
GCATCACCTGGGTTTCGAAGAATCCTTCGTTCTGGTAGCCGGATATGAGGATTTGCTTGTCGGGCTTTGTGA
3457------------------------------------------------------------------3528
AATATCGGATAGGTAGAATTACTATGTGGCATCGGCTTGGATAGAAATGGATGTCATATGGTGCGTGTACAA
3529------------------------------------------------------------------3600
GTAGCTCGTAATAATTTGGGTTGTGTTGCAGTTGTATCGTTGCGTTTAGTACGTCTCCTGTAAAATATAATT
3601------------------------------------------------------------------3672
TCGGGTTACTGGAAAATAACAGNGGTTCGGGCTCTTCGATTTGCGTTACCACTTCAAACTGAACTATTAAAT
3673------------------------------------------------------------------3744
ATTTCGGTAGATTTTCCGTTGTTAGTAAAGAAGGGATTTGCTCGCAGCATACAGTGGCTAGTGTTCCAAAAA
3745------------------------------------------------------------------3816
                                                                      E
                                                                      c
                                                                      o
                                                                      R
                                                                      I
CTTTTTCTTTGTTTTTGACGAGACCGAGATTTTCAATGTTAATCGAGAATTC (SEQ. ID NO:8)
3817---------------------------------------------3868
```

FIG. 3-5

HUMAN HERPESVIRUS TYPE 6 PROTEIN P100, THE CORRESPONDING DNA SEQUENCES, THEIR PREPARATION AND USE

This is a division of application Ser. No. 08/266,311, filed Jun. 27, 1994, which is a continuation application of Ser. No. 08/126,435, filed Sep. 24, 1993, now abandoned, which is a continuation application of Ser. No. 07/908,041, filed Jul. 6, 1992, now abandoned.

The present invention relates to the human herpesvirus type 6 protein p100 and parts thereof having its specific immunological properties. It further relates to antibodies specifically reacting with the protein or parts thereof and to DNA sequences encoding said protein or parts thereof, to recombinant vectors containing these DNA sequences and to host organisms transformed with these vectors. Furthermore, it relates to the preparation of the proteins and DNA sequences and their use in pharmaceutical or diagnostic comnpositions.

The human herpesvirus type 6 (HHV-6) has recently been shown to be closely related to human cytomegalovirus (HCMV) on the basis of amino acid sequence homology (Littler et al., 1990; Lawrence et al., 1990; Chang and Balachandran, 1991; Neipel et al., 1991), genomic position and orientation of conserved herpesvirus genes (Neipel et al., 1991), and antigenic properties (Larcher et al., 1988 Yamamoto et al., 1990; Littler et al., 1990). Until today, only two proteins of HHV-6 and their genes have been described in more detail: the major capsid protein (MCP) (Littler et al., 1990) with a molecular weight of 135 kda, and a phosphoprotein of 41 kda termed HHV-6 p41 (Chang and Balachandran, 1991). The latter one is homologous to UL44 of HCMV.

In order to be able to distinguish infections caused by HHV6 and HCMV it is desirable to have a reagent which is specific for the human herpesvirus type 6.

Thus, the technical problem underlying the present invention essentially is to provide a protein having immunogenic properties and the capability to induce the formation of antibodies lacking crossreactivity with HCMV and other human herpesviruses. Furthermore, it is a technical problem to provide the corresponding DNA sequences.

The solution to this technical problem is achieved by providing the embodiments characterized in the claims.

The present invention therefore relates to a DNA sequence encoding the HHV-6 (human herpesvirus type 6) protein p100 having the amino acid sequence given in FIG. 3 (SEQ ID NO:1) starting from the position corresponding to nucleotide 639 to the position corresponding to nucleotide 3248.

The protein p100 is a structural protein from human herpesvirus type 6 with a molecular weight of about 100 kda that is in part homologous to pp150 of HCMV. It can be obtained by expression of the gene which is located in the region of the EcoRI fragments 6/7 of HHV-6 strain U1102 (distance to the left end of the HHV-6 genome 21–25 kb). The protein p100 has immunogenic properties and lacks crossreactivity with human cytomegalovirus and other human herpesviruses (Yamamoto et al., 1990). It can, therefore, be used as a reagent for detecting HHV-6 antibodies and for the differential diagnosis of HHV-6 infection versus CMV-infection.

The present invention further relates to the corresponding DNA sequence given in FIG. 3 (SEQ ID NO:2) from position 639 to position 3248.

A DNA sequence encoding p100 can be isolated from an HHV-6 genome, as disclosed herein. If the obtained DNA sequence differs from the DNA sequence given in FIG. 3, the above DNA can be derived therefrom by conventional in vitro mutagenesis techniques. Furthermore, the person skilled in the art equipped with the technical teaching disclosed herein will be able to obtain the DNA sequences of the present invention by conventional DNA synthesis techniques.

In a further embodiment, the present invention relates to a DNA sequence hybridizing to the above DNA sequence and encoding a protein having the specific immunological properties of the HHV-6 protein p100. In this context, the term "hybridization" refers to conventional hybridization conditions, preferably to hybridization conditions under which the $T_m$ value is between $T_m=-20°$ to $T_m=-27°$ C. Most preferably, the term "hybridization" refers to stringent hybridization conditions. The term "having the specific immunological properties" characterizes the entire protein defined by the amino acid sequence in FIG. 3 as well as parts of this protein which react with antibodies specific for the protein and substantially without crossreactivity to components of human cytomegalovirus and other herpesviruses. Examples of such immunogenic parts or epitopes of the protein are the amino acid sequences encoded by the nucleotide sequence given in FIG. 3 from position 2960 to position 3141 (SEQ ID NO:3) or the nucleotide sequence given in FIG. 3 from position 2408 to position 2959 (SEQ ID NO:4). These epitopes may also be used in the diagnostic composition described below.

The present invention further relates to recombinant vectors containing the above DNA sequences whereby the DNA sequences may be under the control of a homologous or heterologous promoter allowing its expression in a desired host cell.

A further embodiment of the present invention is a host organism transformed with one of the recombinant vectors of the present invention wherein the host organism is a bacterium, preferably of the genus Escherichia, a yeast, preferably of the genus Saccharomyces, a plant cell or an animal cell, preferably a mammalian cell.

The present invention also relates to the preparation of the HHV-6 protein p100 which comprises the steps of cultivating a transformed host organism and recovering said protein from the culture.

A further object of the present invention is to provide antibodies specifically reacting with the HHV-6 protein p100 or parts thereof having its specific immunological properties but not with components of human cytomegalovirus and other herpesviruses. The person skilled in the art provided with the proteins and fragments thereof of the present invention can produce these antibodies according to conventional methods. In a preferred embodiment of the antibodies of the present invention, the antibodies are monoclonal antibodies.

Another object of the invention is to provide pharmaceutical compositions containing the HHV-6 protein p100 or parts thereof having its specific immunological properties and/or antibodies directed to them, wherein the pharmaceutical compositions are suitable for the prophylaxis or treatment of HHV-6 infections.

A further object of the invention is to provide a composition containing the HHV-6 protein p100 or parts thereof having its specific immunological properties or the corresponding DNA sequences or antibodies of the invention. These compositions may additionally contain parts of the major capsid protein gene of HHV-6, especially the DNA sequences given in FIG. 1 (SEQ ID NOS:5 and 6) and/or the polypeptide being encoded by these DNA sequences or parts of the gene encoding the phosphorylated HHV-6 protein of 41 kda, especially the DNA sequence given in FIG. 2 (SEQ ID NO:7) and/or the polypeptide being encoded by these DNA sequences. Since the HHV-6 protein p100 has the capability to induce the formation of antibodies lacking crossreactivity with human cytomegalovirus or human herpesviruses, it may be used in the differential diagnosis for distinguishing whether an infection is caused by HHV-6 or human cytomegalovirus or other herpesviruses. FIG. 1 shows the sequences of the viral inserts of clones pMF94 (SEQ ID NO:5) and pMF295 (SEQ ID NO:6). Both sequences are part of the major capsid protein gene of HHV-6 as published in (Littler et al. 1990). FIG. 2 shows the sequence of the viral insert of clone pMF90 (SEQ ID NO:7). The sequence is idential with nucleotides 117–194 of the sequence published in (Chang and Balachandran, 1991). FIG. 3 shows the complete sequence of the HHV-6 EcoRI fragments numbered 6 and 7 (starting from the left end) (SEQ ID NO:8). These fragments contain the entire p100 gene of HHV-6. The position of pROS expression clones is indicated within the sequence.

The present invention is explained in more detail in the following description and the figures:

FIG. 1 shows the DNA sequences of the viral inserts of clones pMF94 (SEQ ID NO:5) and pMF295. (SEQ ID NO:6) Both sequences are part of the major capsid protein gene of HHV-6 as published in Littler et al., 1990.

FIG. 2 shows the DNA sequence of the viral insert of clone pMF90 (SEQ ID NO:7). The sequence is identical with nucleotides 117–194 of the sequence published in Chang and Balachandran, 1991.

FIGS. 3A–3E show the complete DNA sequence of the HHV-6 EcoRI fragments numbered 6 and 7 (starting from the left end) (SEQ ID NO:8). These fragments contain the entire p100 gene of HHV-6. Furthermore, the amino acid sequence of p100 is shown, SEQ ID NO:1.

Figure 4:
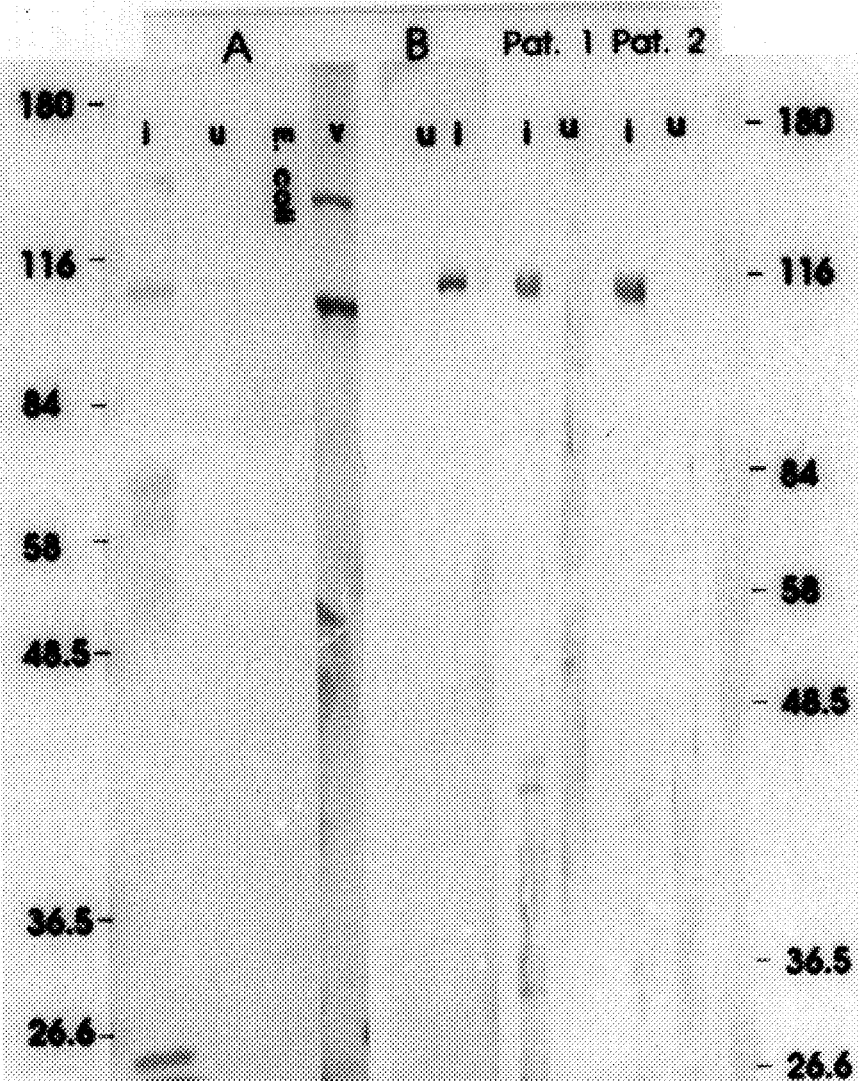

FIG. 4 shows a Western blot analysis wherein antiserum of rabbits immunized with HHV-6 infected HSB-2 cells and antibodies against thie HHV-6 protein p100 purified from this antiserum are reacted with viral proteins.

Figure 5:
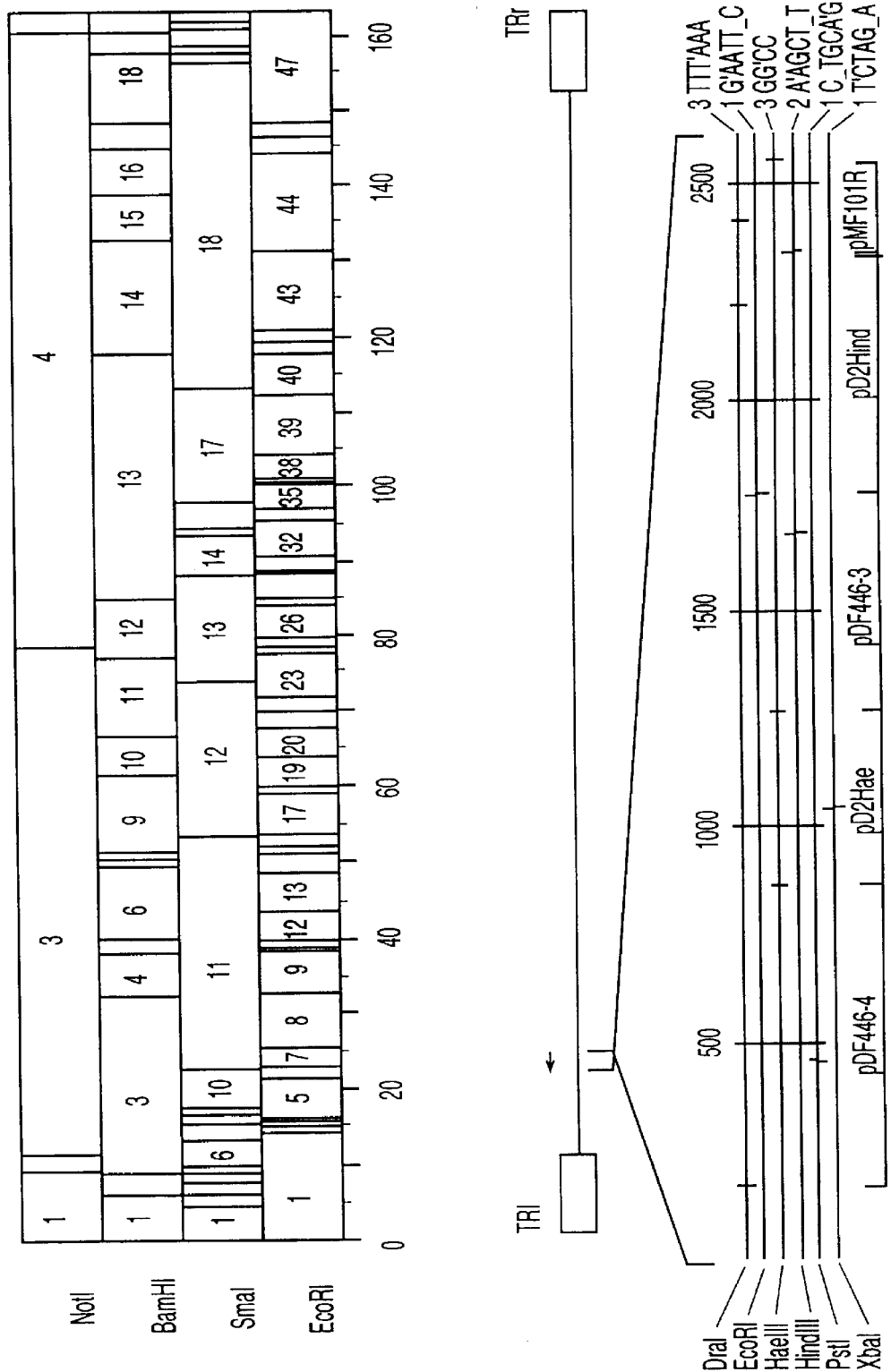

FIG. 5 shows the restriction map of the HHV-6 genome.

Figure 6:
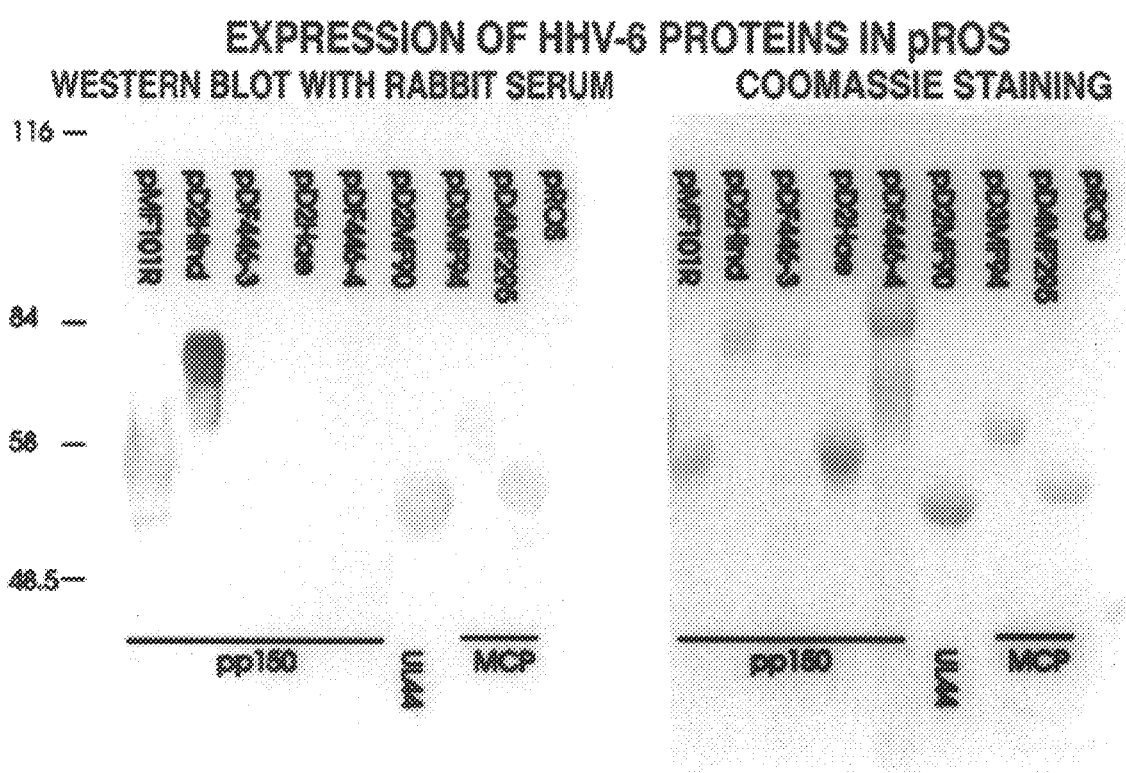

FIG. 6 shows the results of the expression of HHV-6 proteins in the expression vector pROS in a Western blot with rabbit serum and a PAGE Coomassie staining.

Figure 7:
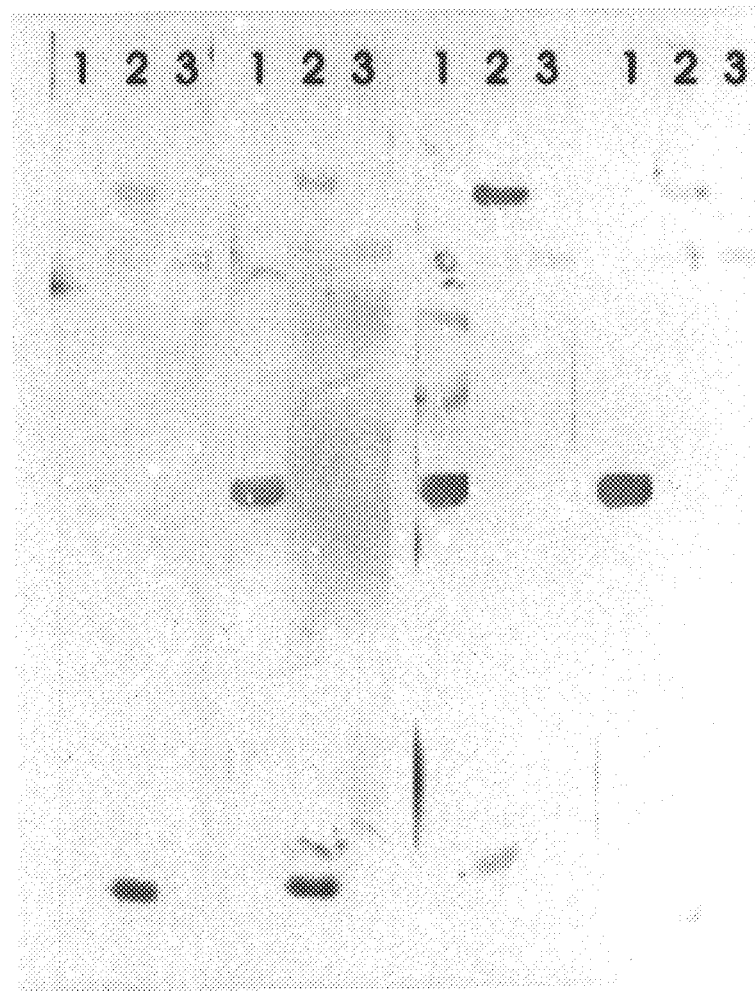

FIG. 7 shows the reactivity of the serum of four patients with HHV-6 epitopes.

The DNA sequences encoding the immunogenic proteins and parts thereof were identified in a genomic HHV-6 gene bank with mono- and polyspecific rabbit antisera against HHV-6 proteins.

Rabbits were immunized with whole HHV-6 infected HSB-2 cells. The obtained antiserum reacted with at least 7 viral proteins (FIG. 4). Antibodies against a 100 kda protein of HHV-6 were purified from this serum. For this purpose, entire viral protein was subjected to preparative SDS polyacrylamide electrophoresis. Viral protein with a molecular weight of 100 kda was transferred to nitrocellulose membranes and incubated with the diluted rabbit serum. Antibodies that were specifically bound on the nitrocellulose sheets were eluted with 100 mM glycin at pH 2.7. The obtained antibodies reacted specifically with an HHV-6 virion protein of about 100 kda (FIG. 4). Both serum preparations were used to screen the genomic library.

The construct of a genomic library DNA from cosmids containing the entire HHV-6 genome in overlapping fragments was sheared by sonication. After addition of EcoRI linkers, EcoRI digestions and size fractionation it was ligated into the commercially available vector lambda zapII (Stratagene Inc., La Jolla, USA). After in vitro packaging a gene bank of $3 \times 10^5$ independent recombinants was obtained. Positive clones were identified by immunological screening using the sera mentioned and a commercially available detection system ('Pico blue', Stratagene Inc., La Jolla, USA). The identified lambda clones were then subcloned into the Bluescript SK- vector by 'in vivo excision' following the supplier's instructions (Stratagene Inc.). Four clones that were especially reactive in Western blots (pMF101, pMF90 (SEQ ID NO7), pMF94 (SEQ ID NO:5), pMF295 (SEQ ID NO:6)) were chosen for further characterization. The inserts of these clones were sequenced by Sanger's chain termination method. Data were analyzed by the Genetics Computer Group (GCG, Madison, Wisc., USA) sequence analysis package. The predicted amino acid sequences were used for homology searches with the computer program FASTA (Pearson & Lipman, 1988) in a library containing all of the published herpesvirus sequences. The clones pMF94 (SEQ ID NO:5) and pMF295 (SEQ ID NO:6) were found to contain parts of the published Major Capsid Protein gene of HHV-6 (FIG. 1) (Littler et al., 1990), while pMF90 (SEQ ID NO:7) contains part of an open reading frame homologous to UL44 of HCMV (FIG. 2). The corresponding HHV-6 gene has recently been identified using monoclonal antibodies against a phosphorylated HHV-6 protein of 41 kda (Chang and Balachandran, 1991). However, the epitope identified by Chang et al. is located after amino acid 227 of their sequence, while pMF90 (SEQ ID NO:7) covers amino acids 119–187 only. No homologous gene could be found for the predicted amino acid sequence of clone pMF101. The insert of pMF101 was used to locate the gene within the virus genome. By hybridization with 7 cosmid clones that encompass the entire HHV-6 genome (Neipel et al., 1991) it could be located within an 1.4 kb EcoRI fragment close to the left terminal repeat (FIG. 5). Further sequencing in this area revealed an open reading frame coding for a protein of 870 amino acids with a predicted molecular weight of 97 kda (termed p100 hereinafter).

Five fragments of p100, comprising almost the complete protein (pDF446-4 (SEQ ID NO:9), pDF446-3 (SEQ ID NO:10), pD2Hae (SEQ ID NO:11), pD2Hind (SEQ ID NO:12), pMF101R (SEQ ID NO:13), were prokaryotically expressed as β-galactosidase fusion protein in the vector pROS (Ellinger et al). In Western blot assays only the carboxyterminal clones reacted with both rabbit human HHV-6 positive sera (FIG. 6, FIG. 7). Fusion protein expressed from pMF101R (SEQ ID NO:13) was used to purify antibodies from rabbit serum as described above. The antibodies were used to carry out Western blot analyses with HHV-6 infected and uninfected HSB-2 cells. A protein of 100 kda was detected in infected cells only. Of all expression clones investigated so far the carboxyterminal parts of p100 were most reliably recognized by human HHV-6 positive sera in Western blot analyses. Since it would be possible only with great technical elaboration to isolate virion proteins in the amounts necessary for diagnostic aids, the manner of preparation by gene manipulation according to the invention is especially advantageous. In Western blot analyses using HHV-6 infected cells a protein of 100 kda is recognized most reliably by human sera. It could not have been expected that prokaryotically expressed p100 or parts thereof are invariably recognized by human sera, as the homologous gene of HCMV codes for a much larger protein, and the immunogenic parts of the HHV-6 gene did not show any homology to HCMV pp150. It is also surprising that the prokaryotically expressed part of an phosphorylated HHV-6 protein homologous to HCMV UL44 (pMF90 (SEQ ID NO:7)) is recognized by most HHV-6 positive human sera.

It is possible according to the invention to use p100 and/or the fragment of the UL44 homologue of HHV-6 (pMF90 (SEQ ID NO:7)) and/or the phosphorylated HHV-6 protein of 41 kD, or immunogenic parts thereof, which have been prepared in prokaryotic or eukaryotic cells, for example yeast cells, human or animal cells, as a reagent for detecting HHV-6 antibodies, for example in an ELISA assay.

EXAMPLE

A fragment of 182 bp from the carboxyterminal part of HHV-6 p100 (nucleotides 2960–3141 in FIG. 3) was ligated in the expression vector pROS (Ellinger, S. et al., 1989). The clone is termed pMF101R (SEQ ID NO:13). The BamHI-HindIII fragments from plasmid pMF90 (SEQ ID NO:7), pMF94 (SEQ ID NO:5), and pMF295 (SEQ ID NO:6) were also ligated into pROS. They are termed pD2MF90, pD2MF94, and pD2MF295, respectively. Transformation of the resulting hybrid plasmid into *E. coli* JK50 was followed by isolation of clones whose plasmid DNA had the expected restriction pattern. After induction of the lac promoter with isopropyl-β-D-thiogalacto-pyranoside (IPTG) the clones expressed large amounts of a fusion protein having a viral fraction. The fusion proteins were isolated from the bacterial cells and used in Western blotting experiments. All human sera that were HHV-6 positive in a standard immunofluorescence assay using HHV-6 infected HSB-2 cells recognized at least one of the fusion proteins (FIG. 6). Human sera that were found to be HHV-6 negative using the immunofluorescence did react weakly or not at all.

Thus, prokaryotically expressed parts of p100 or the UL44 homologue of HHV-6 can be used in a diagnostic assay that is more sensitive and specific than the immunofluorescence used so far.

References

Chang, C. K. and Balachandran, N. (1991) Identification, Characterization, and Sequence Analysis of a cDNA Encoding a Phosphoprotein of Human Herpesvirus 6. J. Virol., 65:2884–2894.

Larcher, C., Huemer, H. P., Margreiter, R., and Dierich, M. P. (1988) Serological crossreaction of human herpesvirus-6 with cytomegalovirus [letter]. Lancet, 2:963–964.

Lawrence, G. L., Chee, M., Craxton, M. A., Gompels, U. A., Honess, R. W., and Barrell, B. G. (1990) Human herpesvirus 6 is closely related to human cytomegalovirus. J. Virol., 64:287–299.

Littler, E., Lawrence, G., Liu, M. Y., Barrell, B. G., and Arrand, J. R. (1990) Identification, cloning, and expression of the major capsid protein gene of human herpesvirus 6. J. Viral., 64:714–722.

Neipel, F., Ellinger, K., and Fleckenstein, B. (1991) The unique region of the human herpesvirus type 6 genome is essentially colinear to the UL segment of human cytomegalovirus. J. Gen. Virol., Yamamoto, M., Black, J. B., Stewart, J. A., Lopez, C., and Pellett, P. E. (1990) Identification of a nucleocapsid protein as a specific serological marker of human herpesvirus 6 infection. J. Clin. Microbiol., 28:1957–1962.

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 870 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met  Asp  Leu  Gln  Arg  His  Pro  Ile  Pro  Phe  Ala  Trp  Leu  Asp  Arg  Asp
 1                    5                        10                       15

Lys  Val  Glu  Arg  Leu  Thr  Asp  Phe  Leu  Ser  Asn  Leu  Glu  Arg  Leu  Asp
              20                        25                       30

Asn  Val  Asp  Leu  Arg  Glu  His  Pro  His  Val  Thr  Asn  Ser  Cys  Val  Val
              35                        40                       45

Arg  Glu  Gly  Asp  Asp  Val  Asp  Asp  Leu  Lys  Thr  Leu  Tyr  Asn  Leu  Leu
         50                        55                       60

Val  Leu  Trp  Leu  Met  Tyr  His  Tyr  Val  Leu  Ser  Lys  Arg  Lys  Pro  Asp
65                        70                        75                       80

Tyr  Asn  Ala  Ile  Trp  Gln  Asp  Ile  Thr  Lys  Leu  Gln  Ser  Val  Val  Asn
                   85                        90                       95

Glu  Tyr  Leu  Asn  Ser  Lys  Gly  Leu  Asn  Lys  Gly  Ile  Phe  Glu  Asn  Met
```

-continued

|   |   |   |   | 100 |   |   |   |   | 105 |   |   |   |   | 110 |
|---|---|---|---|---|---|---|---|---|---|---|---|---|---|---|

Phe Thr Asn Lys Glu Lys Phe Glu Ser Gln Phe Ser Asp Ile Asn Arg
            115             120             125

Ala Leu Leu Arg Leu Gly Asn Phe Ile Lys Trp Gly Ser Asn Val Ala
130             135                 140

Ile Asp Thr Pro Tyr Val Asn Leu Thr Ala Glu Asp Ser Ser Glu Ile
145             150             155             160

Glu Asn Asn Leu Gln Asp Ala Glu Lys Asn Met Leu Trp Tyr Thr Val
                165             170                 175

Tyr Asn Ile Asn Asp Pro Trp Asp Glu Asn Gly Tyr Leu Ile Thr Ser
            180             185             190

Ile Asn Lys Leu Ile Tyr Leu Gly Lys Leu Phe Leu Ala Leu Thr Gln
            195             200             205

Ser Trp Ser Lys Leu Glu Lys Val Ala Met Ser Gln Ile Val Ile Thr
    210             215             220

Gln Asn His Leu Ser Gly His Leu Arg Arg His Asp Asn Phe Asn Ile
225             230             235             240

Val Tyr Ser His Arg Val Leu Gln Thr Pro Leu Thr Gly Gln Arg Val
            245             250             255

Glu Ser Phe Leu Lys Ile Ile Thr Ser Asp Tyr Asp Ile Ile Lys Ser
            260             265             270

Ser Leu Glu Ser His Ser Ala Ser Lys Ala Phe Ser Met Ser Glu Ile
            275             280             285

Gly Pro Asn Ser Leu Met Asp Phe Val Pro Leu Arg Gly Asp Ile His
            290             295             300

Ser Asn Leu Thr Leu Pro Ser Met Ser Ile Asp Thr Lys Lys Ser Ser
305             310             315             320

Leu Asp Pro Ala Arg Leu Lys Lys Ser Asn Ser Arg Ser Leu Asp Ser
            325             330             335

Phe Leu Arg Met Gln Arg Gln Pro Lys Phe Leu Glu Leu Asp Ser Val
            340             345             350

Asp Asn Ala Gly Glu Lys Ile Leu Leu Lys Glu Ala Thr Leu Gly Gly
            355             360             365

Glu Asn Val Lys Ala Thr Thr Pro Ala Ser Ser Val Ser Leu Met Ser
370             375             380

Gly Val Glu Ser Pro Ser Ser Phe Thr Ser Thr Asn Leu Asp Leu Pro
385             390             395             400

Leu Ser Ser Phe Thr Ser Thr Asn Leu Asp Leu Arg Asp Lys Ser His
            405             410             415

Gly Asn Tyr Lys Ile Gly Pro Ser Gly Ile Leu Asp Phe Asn Val Lys
            420             425             430

Phe Pro Pro Asn Ala Gln Leu Asn Thr Asn Gly Val Asp Leu Leu Gln
            435             440             445

Asp Lys Thr Ser Ile Gly Ser Pro Ser Ser Gly Ile Thr Asp Val Val
    450             455             460

Asn Gly Phe Ala Asn Leu Asn Leu His Gln Asn Lys Ser Asn Val Ser
465             470             475             480

Pro Pro Trp Ser Arg Asn Thr Ala Ala Asn Ala Asp Phe Leu Asp Pro
            485             490             495

Val His Arg Phe Val Pro Glu Gln Thr Gly Thr Pro Phe Val Leu Asn
            500             505             510

Asn Ser Asp Val Ala Gly Ser Glu Ala Lys His Thr Thr Tyr Ser Thr
            515             520             525

| Glu | Thr | Gly | Val | Ser | Pro | Arg | Asn | Val | Phe | Leu | Ile | Lys | Asp | Leu | Arg |
|||||||||||||||||
|  |  | 530 |  |  |  | 535 |  |  |  | 540 |  |  |  |  |  |

Glu Thr Gly Val Ser Pro Arg Asn Val Phe Leu Ile Lys Asp Leu Arg
         530               535              540

Gly Lys Asp Gly Phe Arg Lys Gln Lys Gln Ser Asp Ile Pro Lys Ser
545               550              555              560

Leu Thr Lys Glu Arg Asn Asp Lys Ala Ile Met His Ser Arg Glu Val
         565               570              575

Thr Gly Asp Ser Gly Asp Ala Thr Glu Thr Val Gly Ala Arg Asn Ser
        580               585              590

Pro Ala Leu Arg Lys Ile Lys Gln Ala Asn Asp Phe Phe Ala Gly Leu
         595               600            605

Asn Lys Lys Asn Asp Arg Asp Val Leu Arg Gly Gly Lys Gly Asn Ser
   610                615              620

Lys Asp Leu His Ser Gly Gly Asn Ala Lys Lys Glu Met Ser Gly
625               630              635              Gly 640

Lys Phe Asn Asp Asp Lys Glu Met Thr Arg Asn Gly Gln Glu Pro Ser
             645              650            655

Arg Ser Leu Met Gly Asp Ala Arg Asn Ala Gly Asp Glu Gln Tyr Ile
        660               665              670

Gln Ala Gly Leu Gly Gln Arg Val Asn Asn Leu Leu Ser Gln Phe Thr
        675               680             685

Asn Leu Ile Ser Leu Gly Glu Lys Gly Ile Glu Asp Ile Leu Gln Asn
   690                695            700

Gln Arg Gly Thr Glu Leu Lys Leu Ala Thr Glu Asn Lys Ser Gly Arg
705               710            715              720

Glu Ser Glu Glu Ala Asn Val Glu Lys Ile Leu Glu Val Ser Asn Pro
             725             730           735

Gln Asp Met Phe Lys Asn Phe Arg Leu Gln Asn Asp Leu Asp Ser Val
        740             745           750

Gln Ser Pro Phe Arg Leu Pro Asp Ala Asp Leu Ser Arg Glu Leu Asp
     755               760            765

Ser Ala Ser Phe Lys Asp Ala Leu Asp Leu Lys Leu Pro Gly Asn Gly
   770                775            780

Glu Arg Glu Ile Asp Leu Ala Leu Glu Lys Val Lys Val Gly Glu Thr
785               790            795             800

Glu Thr Ser Asp Leu Lys Val Gly Gln Asp Glu Ser Phe Val Pro Ala
             805             810           815

Gln Leu Met Lys Val Glu Thr Pro Glu Glu Lys Asp Asp Ile Ile Glu
        820             825            830

Gln Met Val Leu Arg Ile Arg Gln Asp Gly Glu Thr Asp Glu Asn Thr
     835               840            845

Val Ser Gly Pro Gly Val Ala Glu Ser Leu Asp Ile Glu Ala Lys Gly
850               855              860

Glu Ser Ala Ile Ala Ser
865               870

(2) INFORMATION FOR SEQ ID NO:2:

(i) SEQUENCE CHARACTERISTICS:
        (A) LENGTH: 2610 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

ATGGATCTGC AAAGACATCC GATTCCGTTT GCGTGGCTAG ATCGAGACAA AGTTGAGCGT   60

```
CTTACAGATT  TTCTCAGCAA  TTTGGAAAGA  CTGGATAATG  TAGATTTGCG  AGAGCATCCC    120

CATGTGACTA  ATTCTTGTGT  CGTGAGAGAG  GGAGACGATG  TAGACGATTT  AAAAACATTG    180

TATAACCTAC  TAGTGTTATG  GCTTATGTAT  CACTACGTCT  TATCTAAAAG  GAAGCCGGAT    240

TATAATGCTA  TATGGCAAGA  CATCACGAAA  CTCCAAAGTG  TCGTAAACGA  GTACTTAAAC    300

TCCAAAGGTC  TGAATAAAGG  AATTTTTGAA  AATATGTTCA  CGAACAAAGA  AAAGTTTGAA    360

TCGCAATTCA  GTGATATTAA  TCGCGCTTTA  CTGCGTTTAG  GAAACTTTAT  TAAGTGGGGT    420

AGCAATGTTG  CGATCGATAC  TCCTTATGTA  AATCTTACTG  CAGAAGACAG  CAGCGAGATA    480

GAAAATAATT  TGCAAGATGC  TGAAAAAAAC  ATGCTGTGGT  ATACCGTCTA  TAACATAAAT    540

GACCCCTGGG  ACGAAAACGG  TTACTTAATA  ACGAGTATTA  ATAAATTAAT  TTATCTCGGT    600

AAGTTATTTT  TAGCGTTAAC  TCAGTCCTGG  TCAAAGCTAG  AAAAGGTTGC  TATGAGTCAA    660

ATTGTAATCA  CGCAAAATCA  TCTCTCGGGT  CATTTGAGGA  GGCACGACAA  TTTTAATATT    720

GTATATTCTC  ATAGGGTTTT  GCAGACTCCT  CTGACTGGTC  AAAGAGTAGA  GAGTTTTCTG    780

AAAATAATCA  CCAGTGATTA  TGATATTATC  AAAAGTAGTC  TGGAATCACA  CAGCGCGTCG    840

AAAGCATTTT  CGATGTCTGA  GATTGGGCCT  AATTCTTTAA  TGGATTTCGT  CCCTTTACGC    900

GGCGATATAC  ATTCAAATTT  GACTTACCT  AGTATGTCTA  TAGATACAAA  GAAATCATCT    960

TTAGATCCGG  CTCGTCTGAA  AAAAAGTAAT  TCCAGAAGTT  TGGATAGTTT  CTTAAGAATG   1020

CAGAGACAAC  CTAAATTTCT  AGAGTTGGAT  AGCGTTGATA  ATGCCGGGGA  AAAAATTTTA   1080

CTAAAGGAAG  CAACACTCGG  GGGTGAAAAC  GTTAAAGCGA  CAACGCCTGC  TTCCTCTGTC   1140

TCTTTAATGT  CCGGAGTTGA  GTCGCCGTCG  TCTTTCACTT  CTACCAATCT  GGATCTGCCG   1200

TTGTCGTCTT  TCACTTCTAC  TAATCTGGAT  CTGCGAGATA  AGTCGCACGG  TAATTATAAA   1260

ATTGGCCCTT  CGGGGATTTT  AGATTTTAAT  GTTAAATTTC  CACCTAATGC  GCAATTGAAT   1320

ACGAACGGTG  TGGATTTACT  ACAGGATAAA  ACTTCGATCG  GGAGTCCCAG  TAGCGGTATT   1380

ACCGATGTGG  TAAATGGTTT  CGCTAATCTC  AATCTGCATC  AGAATAAATC  AAATGTTTCG   1440

CCACCGTGGA  GCAGAAACAC  AGCGGCGAAT  GCGGACTTTT  TAGATCCGGT  GCATCGCTTT   1500

GTTCCTGAGC  AGACAGGGAC  ACCCTTCGTG  TTGAATAATT  CCGACGTGGC  GGGATCAGAA   1560

GCGAAGCATA  CGACTTACAG  TACGGAGACC  GGCGTTTCAC  CCCGTAACGT  TTTTCTCATT   1620

AAAGATTTGA  GAGGCAAAGA  CGGTTTTAGG  AAACAGAAGC  AGTCAGATAT  TCCGAAAAGC   1680

TTAACTAAGG  AAAGAAATGA  TAAAGCTATA  ATGCACTCAC  GCGAGGTGAC  CGGAGATTCT   1740

GGCGATGCGA  CTGAAACTGT  GGGTGCTCGG  AATTCCCCGG  CGTTGAGAAA  AATTAAGCAA   1800

GCAAATGATT  TTTTTGCCGG  GTTAAATAAG  AAAAATGATC  GTGACGTATT  AAGAGGGGGG   1860

AAAGGAAATA  GCAAGGACTT  GCATTCTGGC  GGCAATGCAA  AAAAAAAGA   AATGTCGGGA   1920

AAGTTTAATG  ACGATAAAGA  AATGACGCGA  AACGGACAAG  AGCCATCACG  TAGTTTAATG   1980

GGAGATGCTA  GAAATGCCGG  AGATGAACAA  TATATTCAAG  CGGGTCTCGG  GCAGCGAGTT   2040

AACAATCTTC  TAAGTCAATT  TACAAATCTG  ATTAGTTTAG  GCGAGAAGGG  CATCGAAGAC   2100

ATTTTGCAGA  ATCAGCGCGG  GACCGAGTTA  AAGTTGGCTA  CAGAAAACAA  GTCGGGACGC   2160

GAATCGGAGG  AAGCTAACGT  AGAAAAAATT  CTTGAAGTTA  GTAATCCTCA  AGATATGTTT   2220

AAAAATTTTA  GGTTGCAAAA  CGATCTCGAT  TCCGTTCAGT  CTCCGTTTAG  GCTACCGGAT   2280

GCTGATTTGT  CTCGCGAGTT  AGATTCCGCG  TCATTTAAGG  ACGCGTTAGA  CTTGAAGCTT   2340

CCGGGTAACG  GAGAACGAGA  AATAGATCTC  GCTCTTGAAA  AAGTGAAGGT  AGGCGAGACG   2400

GAAACCTCAG  ATTTAAAAGT  CGGTCAGGAT  GAAAGTTTTG  TTCCTGCGCA  ATTAATGAAG   2460
```

```
GTTGAGACAC  CTGAAGAAAA  AGATGATATA  ATTGAACAGA  TGGTTCTGAG  GATACGTCAA        2 5 2 0

GACGGGGAAA  CTGATGAAAA  CACCGTCTCT  GGGCCGGGAG  TCGCTGAGTC  TTTGGATATA        2 5 8 0

GAAGCCAAAG  GCGAGTCAGC  GATCGCGTCG                                            2 6 1 0
```

( 2 ) INFORMATION FOR SEQ ID NO:3:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Ala  Leu  Asp  Leu  Lys  Leu  Pro  Gly  Asn  Gly  Glu  Arg  Glu  Ile  Asp  Leu
 1              5                        10                       15

Ala  Leu  Glu  Lys  Val  Lys  Val  Gly  Glu  Thr  Glu  Thr  Ser  Asp  Leu  Lys
              20                       25                       30

Val  Gly  Gln  Asp  Glu  Ser  Phe  Val  Pro  Ala  Gln  Leu  Met  Lys  Val  Glu
         35                       40                       45

Thr  Pro  Glu  Glu  Lys  Asp  Asp  Ile  Ile  Glu  Gln  Met  Val
         50                       55                       60
```

( 2 ) INFORMATION FOR SEQ ID NO:4:

( i ) SEQUENCE CHARACTERISTICS:
        ( A ) LENGTH: 552 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
GAATTCCCCG  GCGTTGAGAA  AAATTAAGCA  AGCAAATGAT  TTTTTTGCCG  GGTTAAATAA          6 0

GAAAAATGAT  CGTGACGTAT  TAAGAGGGGG  GAAAGGAAAT  AGCAAGGACT  TGCATTCTGG        1 2 0

CGGCAATGCA  AAAAAAAAAG  AAATGTCGGG  AAAGTTTAAT  GACGATAAAG  AAATGACGCG        1 8 0

AAACGGACAA  GAGCCATCAC  GTAGTTTAAT  GGGAGATGCT  AGAAATGCCG  GAGATGAACA        2 4 0

ATATATTCAA  GCGGGTCTCG  GGCAGCGAGT  TAACAATCTT  CTAAGTCAAT  TTACAAATCT        3 0 0

GATTAGTTTA  GGCGAGAAGG  GCATCGAAGA  CATTTTGCAG  AATCAGCGCG  GGACCGAGTT        3 6 0

AAAGTTGGCT  ACAGAAAACA  AGTCGGGACG  CGAATCGGAG  GAAGCTAACG  TAGAAAAAAT        4 2 0

TCTTGAAGTT  AGTAATCCTC  AAGATATGTT  TAAAAATTTT  AGGTTGCAAA  ACGATCTCGA        4 8 0

TTCCGTTCAG  TCTCCGTTTA  GGCTACCGGA  TGCTGATTTG  TCTCGCGAGT  TAGATTCCGC        5 4 0

GTCATTTAAG  GA                                                                5 5 2
```

( 2 ) INFORMATION FOR SEQ ID NO:5:

( i ) SEQUENCE CHARACTERISTICS:
        ( A ) LENGTH: 441 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
GAATTCCTGA  CGCCAGCGCC  ACAGGCCTTG  TTATTTGATA  GTGCCGGGAG  TACGCAGAAG          6 0

TAAAATATCT  TGCTCAGGAT  GGTGGTTTCG  TTCGATGGTC  TGTCATTGTC  GGTAAAGACG        1 2 0
```

| | | | | | |
|---|---|---|---|---|---|
|ACGCTTGAAT|CTATTAGATT|CATTCTTTGC|ACATCGGATA|TTTCGTAATT|TCTAACTCTT|180|
|ACGGTGTTCT|GTGTCAGTGG|TGTATCATCC|GCTGTTATTT|TTGCATTCGT|GTCGTTTCTG|240|
|GGCATGGTAT|GGACGAACGG|GCAGAACAGA|CGTCCGTCGA|ACAACGCGTT|GGCGAAATTC|300|
|ACCAGAGGTT|CGCCGCAAAG|TTGCTCGTTG|AGGTTGGAGA|TAGAGATTGT|TCTCTTCACT|360|
|AGGCGAATTA|GCGACACAAG|ATTTCTGTAG|TGAGCGAAAG|CTGCTCCCGG|GATCAGTTCG|420|
|TCGCCCATGT|GGTTGGAATT|C| | | |441|

( 2 ) INFORMATION FOR SEQ ID NO:6:

( i ) SEQUENCE CHARACTERISTICS:
        ( A ) LENGTH: 219 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

| | | | | | |
|---|---|---|---|---|---|
|CCGTGTGAAA|TTAAACGACA|CCATGGAAAA|CAACCTACCC|ACCAGCGTTT|TTTTCCACAA|60|
|TAAAGACCAA|GTCGTGCAGC|GAATTGATTT|TGCCGACATA|TTACCGTCGG|TTTGCCATCC|120|
|CATTGTCCAC|GACTCGACCA|TCGTCGAACG|ACTCATGAAA|AGCGAACCAT|TGCCTACCGG|180|
|CCACCGCTTT|TCCCAACTAT|GTCAACTAAA|AATTACCCG| | |219|

( 2 ) INFORMATION FOR SEQ ID NO:7:

( i ) SEQUENCE CHARACTERISTICS:
        ( A ) LENGTH: 205 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| | | | | | |
|---|---|---|---|---|---|
|CCACTTTTTG|AAAGTTTTAT|GAACATCATC|TCGAATCCTG|AGGTTACGAA|GATGTACATT|60|
|CAGCATGATA|GTGATCTGTA|TACGAGGGTT|TTGGTAACGG|CTTCCGATAC|ATGTACACAG|120|
|GCGTCGGTTC|CCTGTGTGCA|CGGACAAGAA|GTGGTGCGAG|ACACCGGGAG|ATCGCCGTTG|180|
|AGGATTGACC|TTGATCATTC|GACCG| | | |205|

( 2 ) INFORMATION FOR SEQ ID NO:8:

( i ) SEQUENCE CHARACTERISTICS:
        ( A ) LENGTH: 3868 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: modified_base
        ( B ) LOCATION: 14
        ( D ) OTHER INFORMATION: /mod_base=OTHER
           / note= "N is unknown."

( i x ) FEATURE:
        ( A ) NAME/KEY: modified_base
        ( B ) LOCATION: 3695
        ( D ) OTHER INFORMATION: /mod_base=OTHER
           / note= "N is unknown."

( x i ) SEQUENCE DESCRIPTION: SEQ ID NO:8:

-continued

| | | | | | |
|---|---|---|---|---|---|
| GAATTCCTAT | GTTNCGCCCC | GTGCTAGATG | TTTTACTTTC | AGTCTTTTTA | CGCCGGTGTA | 60
| AGGTTTTGTA | CCTGATAGTT | GCGATTATAG | CTAGCATGCT | TATACTATAT | GAACAGACTG | 120
| CATGATAGAT | GAAGTAAACT | AACTGACAGA | AAAAACGGTT | GAATGAGAAC | AGTTGCTTTC | 180
| TGTTCACTGT | CATAAAAAAG | ACACACCACA | TGAGCACAAA | ATCGCTAGCA | AAGAGTGTGA | 240
| TGACGTAAAA | TGAAGTAGCG | TTATGTTTTG | CGACTCTGTG | GTAGAGAATC | ATGGTGGTAA | 300
| CCACTATAAT | GATCATGGGG | ATAGATGTGG | TGAGCGTGAT | TCCGGTAACT | GCGCTCTCCA | 360
| TGATTCGTGC | TGTCTTTAGC | GTGGGTGTCG | AGGTACAGGA | AGCATTGCCT | TTGAACTCTT | 420
| CATTGCGCTA | TTAAAGATAT | TGAATGTTAT | TTTCATGTTA | CGCTACATTA | AAATATTCGG | 480
| TAACAATGAT | GTCTGAAGAC | TTACCAGAAG | TTTGGACAGC | TCAATGACAG | TGTCCATCTC | 540
| GTCGCTTGTC | AGTTTTCTGT | GTGGGTAAAA | AAAAGACTAT | TAAACATTGA | ATGTTGGCGG | 600
| AAATGAGCAG | TTCTGTTTTT | GAGTTTGTTT | CTAAAATAT | GGATCTGCAA | AGACATCCGA | 660
| TTCCGTTTGC | GTGGCTAGAT | CGAGACAAAG | TTGAGCGTCT | TACAGATTTT | CTCAGCAATT | 720
| TGGAAAGACT | GGATAATGTA | GATTTGCGAG | AGCATCCCCA | TGTGACTAAT | TCTTGTGTCG | 780
| TGAGAGAGGG | AGACGATGTA | GACGATTTAA | AAACATTGTA | TAACCTACTA | GTGTTATGGC | 840
| TTATGTATCA | CTACGTCTTA | TCTAAAAGGA | AGCCGGATTA | TAATGCTATA | TGGCAAGACA | 900
| TCACGAAACT | CCAAAGTGTC | GTAAACGAGT | ACTTAAACTC | CAAAGGTCTG | AATAAGGAA | 960
| TTTTTGAAAA | TATGTTCACG | AACAAAGAAA | AGTTTGAATC | GCAATTCAGT | GATATTAATC | 1020
| GCGCTTTACT | GCGTTAGGA | AACTTTATTA | AGTGGGGTAG | CAATGTTGCG | ATCGATACTC | 1080
| CTTATGTAAA | TCTTACTGCA | GAAGACAGCA | GCGAGATAGA | AAATAATTTG | CAAGATGCTG | 1140
| AAAAAAACAT | GCTGTGGTAT | ACCGTCTATA | ACATAAATGA | CCCCTGGGAC | GAAAACGGTT | 1200
| ACTTAATAAC | GAGTATTAAT | AAATTAATTT | ATCTCGGTAA | GTTATTTTA | GCGTTAACTC | 1260
| AGTCCTGGTC | AAAGCTAGAA | AAGGTTGCTA | TGAGTCAAAT | TGTAATCACG | CAAAATCATC | 1320
| TCTCGGGTCA | TTTGAGGAGG | CACGACAATT | TTAATATTGT | ATATTCTCAT | AGGGTTTTGC | 1380
| AGACTCCTCT | GACTGGTCAA | AGAGTAGAGA | GTTTTCTGAA | AATAATCACC | AGTGATTATG | 1440
| ATATTATCAA | AAGTAGTCTG | GAATCACACA | GCGCGTCGAA | AGCATTTTCG | ATGTCTGAGA | 1500
| TTGGGCCTAA | TTCTTTAATG | GATTTCGTCC | CTTTACGCGG | CGATATACAT | TCAAATTTGA | 1560
| CTTTACCTAG | TATGTCTATA | GATACAAAGA | AATCATCTTT | AGATCCGGCT | CGTCTGAAAA | 1620
| AAAGTAATTC | CAGAAGTTTG | GATAGTTTCT | TAAGAATGCA | GAGACAACCT | AAATTTCTAG | 1680
| AGTTGGATAG | CGTTGATAAT | GCCGGGGAAA | AAATTTTACT | AAAGGAAGCA | ACACTCGGGG | 1740
| GTGAAAACGT | TAAAGCGACA | ACGCCTGCTT | CCTCTGTCTC | TTTAATGTCC | GGAGTTGAGT | 1800
| CGCCGTCGTC | TTTCACTTCT | ACCAATCTGG | ATCTGCCGTT | GTCGTCTTTC | ACTTCTACTA | 1860
| ATCTGGATCT | GCGAGATAAG | TCGCACGGTA | ATTATAAAAT | TGGCCCTTCG | GGGATTTTAG | 1920
| ATTTTAATGT | TAAATTTCCA | CCTAATGCGC | AATTGAATAC | GAACGGTGTG | GATTTACTAC | 1980
| AGGATAAAAC | TTCGATCGGG | AGTCCAGTA | GCGGTATTAC | CGATGTGGTA | AATGGTTTCG | 2040
| CTAATCTCAA | TCTGCATCAG | AATAAATCAA | ATGTTTCGCC | ACCGTGGAGC | AGAAACACAG | 2100
| CGGCGAATGC | GGACTTTTTA | GATCCGGTGC | ATCGCTTTGT | TCCTGAGCAG | ACAGGGACAC | 2160
| CCTTCGTGTT | GAATAATTCC | GACGTGGCGG | GATCAGAAGC | GAAGCATACG | ACTTACAGTA | 2220
| CGGAGACCGG | CGTTTCACCC | CGTAACGTTT | TTCTCATTAA | AGATTTGAGA | GGCAAAGACG | 2280
| GTTTTAGGAA | ACAGAAGCAG | TCAGATATTC | CGAAAAGCTT | AACTAAGGAA | AGAAATGATA | 2340
| AAGCTATAAT | GCACTCACGC | GAGGTGACCG | GAGATTCTGG | CGATGCGACT | GAAACTGTGG | 2400

```
GTGCTCGGAA TTCCCCGGCG TTGAGAAAAA TTAAGCAAGC AAATGATTTT TTTGCCGGGT      2460
TAAATAAGAA AAATGATCGT GACGTATTAA GAGGGGGGAA AGGAAATAGC AAGGACTTGC      2520
ATTCTGGCGG CAATGCAAAA AAAAAAGAAA TGTCGGGAAA GTTTAATGAC GATAAAGAAA      2580
TGACGCGAAA CGGACAAGAG CCATCACGTA GTTTAATGGG AGATGCTAGA AATGCCGGAG      2640
ATGAACAATA TATTCAAGCG GGTCTCGGGC AGCGAGTTAA CAATCTTCTA AGTCAATTTA      2700
CAAATCTGAT TAGTTTAGGC GAGAAGGGCA TCGAAGACAT TTTGCAGAAT CAGCGCGGGA      2760
CCGAGTTAAA GTTGGCTACA GAAACAAGT CGGGACGCGA ATCGGAGGAA GCTAACGTAG       2820
AAAAAATTCT TGAAGTTAGT AATCCTCAAG ATATGTTTAA AAATTTTAGG TTGCAAAACG      2880
ATCTCGATTC CGTTCAGTCT CCGTTTAGGC TACCGGATGC TGATTTGTCT CGCGAGTTAG      2940
ATTCCGCGTC ATTTAAGGAC GCGTTAGACT GAAGCTTCC GGGTAACGGA GAACGAGAAA       3000
TAGATCTCGC TCTTGAAAAA GTGAAGGTAG GCGAGACGGA AACCTCAGAT TTAAAAGTCG      3060
GTCAGGATGA AAGTTTTGTT CCTGCGCAAT TAATGAAGGT TGAGACACCT GAAGAAAAAG      3120
ATGATATAAT TGAACAGATG GTTCTGAGGA TACGTCAAGA CGGGGAAACT GATGAAAACA      3180
CCGTCTCTGG GCCGGGAGTC GCTGAGTCTT TGGATATAGA AGCCAAGGC GAGTCAGCGA       3240
TCGCGTCGTG ATGTAAAAAA TTTTCTCTGG GGAGTTTCAG GTTGCCAATA AAATGCCCAT      3300
TCTCAGACAG CTTTGCGATT ACGTCTTTTT GTTCATTGTT CTGGCTTGTC ATTCTTTCTA      3360
CATAAAACAG GGTCGCGATA GGTGTGCTTT GAGGCAGGAT CAGATTTGGA GAAAATGAAC      3420
GCAGCGTAAT GTGCAAAGGT GTTCCCGGGG CCCACAGCAT CACCTGGGTT TCGAAGAATC      3480
CTTCGTTCTG GTAGCCGGAT ATGAGGATTT GCTTGTCGGG CTTTGTGAAA TATCGGATAG      3540
GTAGAATTAC TATGTGGCAT CGGCTTGGAT AGAAATGGAT GTCATATGGT GCGTGTACAA      3600
GTAGCTCGTA ATAATTTGGG TTGTGTTGCA GTTGTATCGT TGCGTTTAGT ACGTCTCCTG      3660
TAAAATATAA TTTCGGGTTA CTGGAAAATA ACAGNGGTTC GGGCTCTTCG ATTTGCGTTA      3720
CCACTTCAAA CTGAACTATT AAATATTTCG GTAGATTTTC CGTTGTTAGT AAAGAAGGGA      3780
TTTGCTCGCA GCATACAGTG GCTAGTGTTC CAAAAACTTT TTCTTTGTTT TTGACGAGAC      3840
CGAGATTTTC AATGTTAATC GAGAATTC                                         3868
```

( 2 ) INFORMATION FOR SEQ ID NO:9:

( i ) SEQUENCE CHARACTERISTICS:
        ( A ) LENGTH: 697 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
TAAAACATT GTATAACCTA CTAGTGTTAT GGCTTATGTA TCACTACGTC TTATCTAAAA        60
GGAAGCCGGA TTATAATGCT ATATGGCAAG ACATCACGAA ACTCCAAAGT GTCGTAAACG      120
AGTACTTAAA CTCCAAAGGT CTGAATAAAG GAATTTTTGA AAATATGTTC ACGAACAAAG      180
AAAAGTTTGA ATCGCAATTC AGTGATATTA ATCGCGCTTT ACTGCGTTTA GGAAACTTTA      240
TTAAGTGGGG TAGCAATGTT GCGATCGATA CTCCTTATGT AAATCTTACT GCAGAAGACA      300
GCAGCGAGAT AGAAAATAAT TTGCAAGATG CTGAAAAAAA CATGCTGTGG TATACCGTCT      360
ATAACATAAA TGACCCCTGG GACGAAAACG GTTACTTAAT AACGAGTATT AATAAATTAA      420
TTTATCTCGG TAAGTTATTT TTAGCGTTAA CTCAGTCCTG GTCAAAGCTA GAAAAGGTTG      480
CTATGAGTCA AATTGTAATC ACGCAAAATC ATCTCTCGGG TCATTTGAGG AGGCACGACA      540
```

| | | | | | |
|---|---|---|---|---|---|
| ATTTTAATAT | TGTATATTCT | CATAGGGTTT | TGCAGACTCC | TCTGACTGGT | CAAAGAGTAG | 600
| AGAGTTTTCT | GAAAATAATC | ACCAGTGATT | ATGATATTAT | CAAAAGTAGT | CTGGAATCAC | 660
| ACAGCGCGTC | GAAAGCATTT | TCGATGTCTG | AGATTGG | | | 697

(2) INFORMATION FOR SEQ ID NO:10:

(i) SEQUENCE CHARACTERISTICS:
        (A) LENGTH: 505 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

| | | | | | |
|---|---|---|---|---|---|
| GCCCTTCGGG | GATTTTAGAT | TTTAATGTTA | AATTTCCACC | TAATGCGCAA | TTGAATACGA | 60
| ACGGTGTGGA | TTTACTACAG | GATAAAACTT | CGATCGGGAG | TCCCAGTAGC | GGTATTACCG | 120
| ATGTGGTAAA | TGGTTTCGCT | AATCTCAATC | TGCATCAGAA | TAAATCAAAT | GTTTCGCCAC | 180
| CGTGGAGCAG | AAACACAGCG | GCGAATGCGG | ACTTTTAGA | TCCGGTGCAT | CGCTTTGTTC | 240
| CTGAGCAGAC | AGGGACACCC | TTCGTGTTGA | ATAATTCCGA | CGTGGCGGGA | TCAGAAGCGA | 300
| AGCATACGAC | TTACAGTACG | GAGACCGGCG | TTTCACCCCG | TAACGTTTTT | CTCATTAAAG | 360
| ATTTGAGAGG | CAAAGACGGT | TTTAGGAAAC | AGAAGCAGTC | AGATATTCCG | AAAAGCTTAA | 420
| CTAAGGAAAG | AAATGATAAA | GCTATAATGC | ACTCACGCGA | GGTGACCGGA | GATTCTGGCG | 480
| ATGCGACTGA | AACTGTGGGT | GCTCG | | | | 505

(2) INFORMATION FOR SEQ ID NO:11:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

| | | | | | |
|---|---|---|---|---|---|
| GCCTAATTCT | TTAATGGATT | TCGTCCCTTT | ACGCGGCGAT | ATACATTCAA | ATTTGACTTT | 60
| ACCTAGTATG | TCTATAGATA | CAAAGAAATC | ATCTTTAGAT | CCGGCTCGTC | TGAAAAAAG | 120
| TAATTCCAGA | AGTTTGGATA | GTTTCTTAAG | AATGCAGAGA | CAACCTAAAT | TTCTAGAGTT | 180
| GGATAGCGTT | GATAATGCCG | GGGAAAAAAT | TTTACTAAAG | GAAGCAACAC | TCGGGGGTGA | 240
| AAACGTTAAA | GCGACAACGC | CTGCTTCCTC | TGTCTCTTTA | ATGTCCGGAG | TTGAGTCGCC | 300
| GTCGTCTTTC | ACTTCTACCA | ATCTGGATCT | GCCGTTGTCG | TCTTTCACTT | CTACTAATCT | 360
| GGATCTGCGA | GATAAGTCGC | ACGGTAATTA | TAAAATTGG | | | 399

(2) INFORMATION FOR SEQ ID NO:12:

(i) SEQUENCE CHARACTERISTICS:
        (A) LENGTH: 566 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

| | | | | | |
|---|---|---|---|---|---|
| GAATTCCCCG | GCGTTGAGAA | AAATTAAGCA | AGCAAATGAT | TTTTTGCCG | GGTTAAATAA | 60

-continued

| | | | | | | |
|---|---|---|---|---|---|---|
| GAAAAATGAT | CGTGACGTAT | TAAGAGGGGG | GAAAGGAAAT | AGCAAGGACT | TGCATTCTGG | 120 |
| CGGCAATGCA | AAAAAAAAG | AAATGTCGGG | AAAGTTTAAT | GACGATAAAG | AAATGACGCG | 180 |
| AAACGGACAA | GAGCCATCAC | GTAGTTTAAT | GGGAGATGCT | AGAAATGCCG | GAGATGAACA | 240 |
| ATATATTCAA | GCGGGTCTCG | GGCAGCGAGT | TAACAATCTT | CTAAGTCAAT | TTACAAATCT | 300 |
| GATTAGTTTA | GGCGAGAAGG | GCATCGAAGA | CATTTTGCAG | AATCAGCGCG | GGACCGAGTT | 360 |
| AAAGTTGGCT | ACAGAAAACA | AGTCGGGACG | CGAATCGGAG | GAAGCTAACG | TAGAAAAAAT | 420 |
| TCTTGAAGTT | AGTAATCCTC | AAGATATGTT | TAAAAATTTT | AGGTTGCAAA | ACGATCTCGA | 480 |
| TTCCGTTCAG | TCTCCGTTTA | GGCTACCGGA | TGCTGATTTG | TCTCGCGAGT | TAGATTCCGC | 540 |
| GTCATTTAAG | GACGCGTTAG | ACTTGA | | | | 566 |

(2) INFORMATION FOR SEQ ID NO:13:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

| | | | | | | |
|---|---|---|---|---|---|---|
| CGCGTTAGAC | TTGAAGCTTC | CGGGTAACGG | AGAACGAGAA | ATAGATCTCG | CTCTTGAAAA | 60 |
| AGTGAAGGTA | GGCGAGACGG | AAACCTCAGA | TTTAAAAGTC | GGTCAGGATG | AAAGTTTTGT | 120 |
| TCCTGCGCAA | TTAATGAAGG | TTGAGACACC | TGAAGAAAAA | GATGATATAA | TTGAACAGAT | 180 |
| GG | | | | | | 182 |

We claim:

1. An antibody specifically reacting with a HHV-6 (human herpesvirus type 6) protein p100 or a part of a HHV-6 protein p100 having its specific immunological properties, wherein said HHV-6 protein in p100 has the amino acid sequence given in FIG. 3, but not with the components of human cytomegalovirus and other herpesviruses.

2. The antibody according to claim 1 which is a monoclonal antibody.

3. A composition containing an antibody according to claim 1 in combination with a pharmaceutically acceptable carrier or diluent.

4. A composition comprising an antibody according to claim 1.

5. A method for the diagnosis of herpesvirus virus type 6 (HHV-6) infection, wherein said method comprises:

(a) contactng an antibody of claim 1 or 2 with a biological sample and (b) detecting the immunological complexes formed between the antibody and HHV-6 p100 protein, wherein the presence of immunological complexes is indicative of the presence of HHV-6 in the biological sample.

6. The method of claim 5, wherein said method comprises an ELISA.

7. The method of claim 5, wherein said method comprises a Western blot.

8. A method for producing an antibody of claim 1 or 2, wherein said method comprises:

(a) immunizing a mammal with a herpesvirus virus type 6 p100 protein, and (b) recovering said antibodies.

* * * * *